(12) United States Patent
Matsui et al.

(10) Patent No.: US 6,458,074 B1
(45) Date of Patent: Oct. 1, 2002

(54) ENDOSCOPE

(75) Inventors: Raifu Matsui, Hino; Keiichi Arai, Hachioji; Ryuta Sekine, Chofu, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 121 days.

(21) Appl. No.: 09/615,275

(22) Filed: Jul. 13, 2000

(30) Foreign Application Priority Data

Feb. 3, 2000 (JP) ........................................ 2000-026257

(51) Int. Cl.[7] .................................................. A61B 1/00
(52) U.S. Cl. ........................ 600/106; 600/104; 600/107
(58) Field of Search ................................ 600/104–107, 600/129, 153

(56) References Cited

U.S. PATENT DOCUMENTS 4,436,087 A * 3/1984 Ouchi ........................ 600/107

FOREIGN PATENT DOCUMENTS

| JP | 405184534 A | * | 7/1993 | .................. 600/104 |
| JP | 409234182 A | * | 9/1997 | ............ A61B/1/00 |
| JP | 2000-37348 | | 2/2000 | |

* cited by examiner

*Primary Examiner*—John Mulcahy
(74) *Attorney, Agent, or Firm*—Frishauf, Holtz, Goodman & Chick, P.C.

(57) ABSTRACT

An endoscope is provided which has a first forceps raising base and a second forceps raising base. The first forceps raising base is provided at a distal end opening of a first treating tool insertion channel formed at a distal end of an insertion section, and is adapted to be raised in a first direction. The second forceps raising base is provided at a distal end opening of a second treating tool insertion channel formed at the distal end of the insertion section, and is adapted to be raised in a second direction different from the first direction. The first and second raising directions of the first and second forceps raising bases are different from each other in at least two combinations.

9 Claims, 2 Drawing Sheets

ENDOSCOPE

CROSS-REFERENCE TO RELATED APPLICATIONS

This application is based upon and claims the benefit of priority from the prior Japanese Patent Application No. 2000-026257, filed Feb. 3, 2000, the entire contents of which are incorporated herein by reference.

BACKGROUND OF THE INVENTION

The present invention relates to an endoscope having a plurality of treating tool insertion channels and adapted to perform a treating operation by treating tools projected from corresponding distal end openings of the corresponding treating tool insertion channels.

The procedure for treating a region in a body cavity of a human subject with the use of a combination of an endoscope having a treating tool insertion channel and treating tool having a treating means has conventionally been carried out widely. In particular, the procedure for resecting a carcinomatous legion in the body cavity with the use of a combination of the endoscope and associated treating tool has been widely accepted.

The procedure comprises raising a diseased tissue region through the injection of a given liquid by an injection needle, resecting that raised portion by a cutting tool and stopping the bleending of a given region, if any, by a blood stopping tool, and so on. At each procedure, a special-use treating tool is inserted through a corresponding treating tool insertion channel of the endoscope and each treating operation is done individually.

As such treating method, Japanese Patent Publication No. 2000-37348 has proposed a new treating system according to which a treating operation is done with an endoscope having two treating tool insertion channels, while inserting corresponding treating tools through the treating tool insertion channels.

In the endoscope of the above-mentioned Japanese Patent Application, a forceps raising device is provided at a distal end opening of one treating tool insertion channel and adapted to be raised away from a distal end opening of the other treating tool insertion channel and the procedure is carried out using a combination of grasping forceps inserted through the treating tool insertion channel, that is, the channel with the forceps raising device attached thereto, and a cutting tool, such as an electric surgical knife, inserted through the above-mentioned other treating tool insertion channel. For example, a diseased mucosa portion or its neighborhood is grasped by the grasping forceps and, by the forceps raising device, the grasping forceps is moved away from the above-mentioned other treating tool insertion channel through which the cutting tool is inserted. By doing so, the mucosa is pulled upwardly and the upwardly. pulled mucosa region is resected by the cutting tool projected from the above-mentioned other treating tool insertion channel.

Such a technique using the combination of the endoscope and treating tools is effective to the case where a pliable mucosa tissue is pulled upwardly and the upwardly pulled mucosa is resected by the treating tool but not effective to the case where a cut is made down to a mucosa layer portion underlying that mucosa. The reason is that it is not possible to cut open the underlying mucosa layer by the raising operation of the grasping forceps.

Further, the specification of the above-mentioned Japanese Patent Application discloses nothing about the technique of guiding the forward end of the cutting tool to a region of interest of a human subject. In the structure of the above-mentioned Application, it is necessary to locate a forward end of the cutting tool by, for example, bending the distal end portion of the insertion section of the endoscope and do so simply by an indirect operation.

When such an operation is done, the grasping forceps at the above-mentioned other treating tool insertion channel and visual field observed under the endoscope are often moved at a time in the locating operation of the cutting tool's forward end. This requires a readjusting operation repeatedly and a cumbersome separating/cutting operation.

BRIEF SUMMARY OF THE INVENTION

It is accordingly the object of the present invention to provide an endoscope which has a plurality of treating tool insertion channels and ensures an easy and positive treating operation by projecting treating tools from distal end openings of the treating tool insertion channels.

The object of the present invention is achieved by the endoscope as will be set out below. That is, the endoscope of the present invention comprises an insertion section having a first treating tool insertion channel and a second treating tool insertion channel, each having a distal end opening at the distal end of the insertion section to allow insertion of a treating tool; a first mechanism provided at the distal end opening of the first treating tool insertion channel and having an operation member for changing a projecting direction of the treating tool projected through the distal end opening toward a first direction; and a second mechanism provided at the distal end opening of the second treating tool insertion channel and having an operation member for changing the projecting direction of the treating tool projected from the distal end opening toward a second direction different from the first direction.

According to the endoscope of the present invention, it is possible to easily and positively resect a wider-range affected region of interest at a time with the use of a combination of an endoscope and associated treating tools, ensure an easier operation and rapidly and positively perform an operation on a region of interest. As a result, less burden is placed on both the operator and patient.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
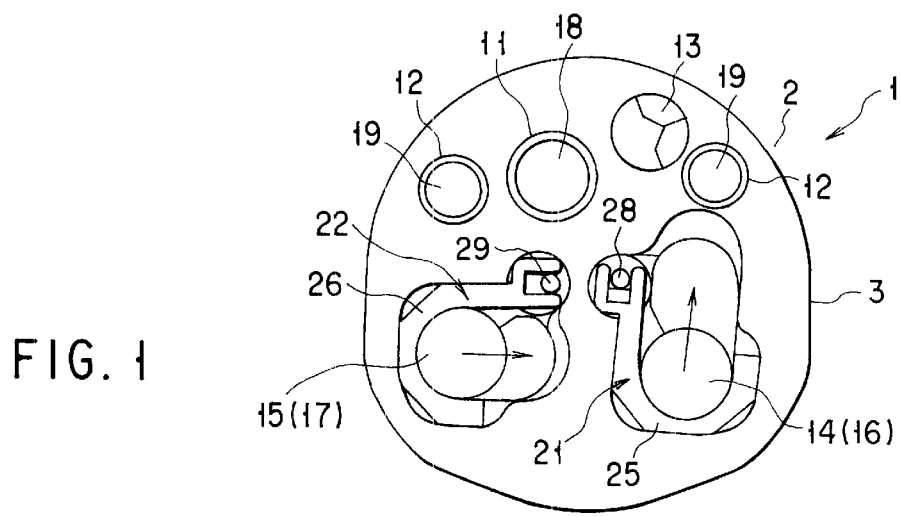
FIG. 1 is a front view showing a distal end of an insertion section of an endoscope according to a first embodiment of the present invention.
Figure 2:
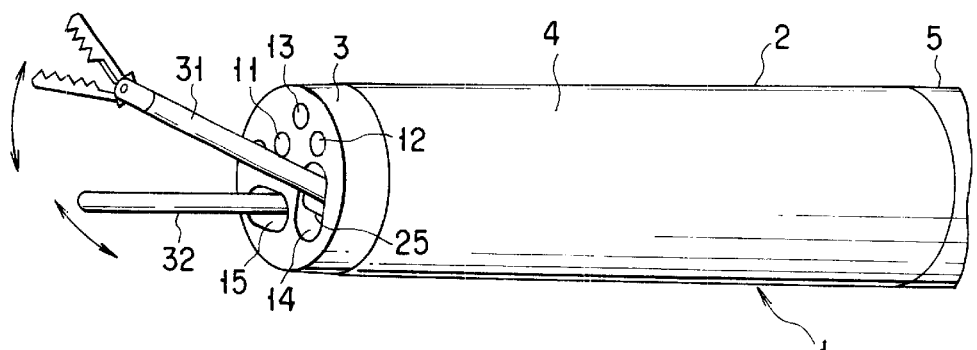
FIG. 2 is a perspective view showing an insertion section of the endoscope.

With reference to FIGS. 1 to 6 an explanation will be made below about an endoscope according to a first embodiment of the present invention. FIG. 1 is a front view showing a distal end face of an insertion section 2 of the endoscope 1 and FIG. 2 is a perspective view showing the distal end and its neighboring portion of the insertion section of the endoscope 1.

As shown in FIG. 2, the insertion section of the endoscope 1 has a distal end 3, bendable portion 4 and flexible tube section 5 sequentially provided in one line from the forward end of the endoscope as in the case of an ordinary endoscope and is pliable as a whole. The bendable section 4 of the insertion section 2 is bendable by the operation of an angle knob provided at an operation section, not shown, connected to a proximal end of the insertion section. By bending the bendable section 4, the distal end 3 of the insertion section 2 can be directed toward an up-down and a right/left direction.

As shown in FIG. 1, an observation optical system 11, two illumination optical systems 12, air/water supply nozzle 13 and distal end opening 16, 17 of channels 14, 15 for allowing two treating tools to be inserted are provided at the distal end face of the insertion section 2.

The observation optical system 11 is comprised of an optical lens including an observation window 18 to allow a body cavity's visual field image to be formed on an image pickup device, not shown, mounted behind it. The illumination optical system 12 is comprised of an illumination lens including an illumination window 19 and mounted at a distal end of a light guide fiber (not shown) for guiding illumination light to the visual field in the body cavity of a human subject.

The air/water supply nozzle 13 is opened in a direction toward an outer surface of the observation window 18 of the observation optical system 11 and adapted to supply a jet of washing water to the outer surface of the observation window 18 and supply the air to it. The two channels 14, 15 for the insertion of the treating tools are used to guide corresponding treating tools therein to allow them to be projected forwardly via their distal end openings 16, 17.

Raising mechanisms 21 and 22 are provided at the distal end openings 16 and 17 to restrict the projecting directions of the corresponding treating tools. When the raising mechanisms 21 and 22 are not operated, the treating tools are projected in substantially the same direction from the distal end openings 16 and 17 and set substantially parallel to the axial direction of the insertion section 2. That is, the distal end opening 16 of the first treating tool insertion channel 14 and distal end opening 17 of the second treating tool insertion channel 15 are set in substantially the same direction and, when a raising operation member (raising base 25) of the first forceps raising mechanism 21 and raising operation member (raising seat or base 26) of the second forceps raising mechanism 22 are set in a standby position before a raising operation, the treating tools are projected in a substantially parallel direction from the distal end openings 16 and 17 of the first and second treating tool insertion channels 14 and 15, respectively.

Figure 3:
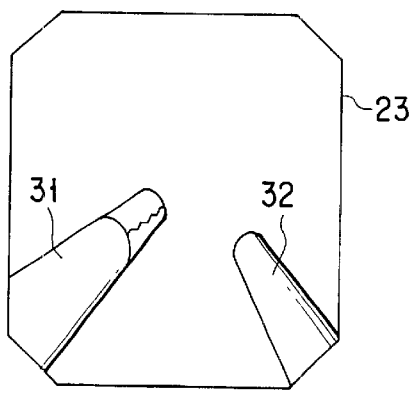
FIG. 3 is a view showing an image of an endoscope's visual field displayed on a TV monitor.

The positions of the distal end openings 16 and 17 of the treating tool insertion channels 14 and 15 are so set that, relative to an endoscopic image seen on a TV monitor, not shown, they are situated at a lower area in a visual field image 23 of the endoscope. Therefore, those treating tools 31 and 32 inserted through the treating tool insertion channels 14 and 15 are situated at both lower right/left areas in the endoscope's visual field image on the TV monitor as shown in FIG. 3.

The raising mechanisms 21 and 22 are provided at the distal end openings 16 and 17 of the treating tool insertion channels 14 and 15. These mechanisms 21 and 22 have direction adjusting functions to control the direction variation of the treating tools projected from the distal end openings 16 and 17.

The raising mechanisms 21 and 22 have raising bases 25 and 26 for supporting the side surface portions of the treating tools trying to be projected from the distal end openings 16 and 17 of the treating tool insertion channels 14 and 15. Like the ordinary endoscope, the raising bases 25 and 26 have their base end portions pivotally supported by pins, not shown. The forward ends of raising operation wires 28 and 29 are connected to the raising (swinging) forward end portions of the raising bases 25 and 26.

The raising operation wires 28 and 29 are individually guided to a proximal-side operation section through wire guide sheaths, not shown, in the insertion section 2. By the operations of the raising operation mechanisms at the operation section it is possible to move the raising operation wires 28 and 29 forward and backward. By pulling the raising operation wires 28 and 19, the raising bases 25 and 26 are swingably raised in accordance with amounts of backward movement of the raising operation wires 28 and 29. The raising amounts of the raising bases 25 and 26 vary in accordance with the amounts by which the operation wires 28 and 29 are pulled. The raising bases 25 and 26 are independently operated by individually operating the raising operation wires 28 and 29.

The treating tools 31 and 32 projected from the distal end openings 16 and 17 of the treating tool insertion channels 14 and 15 are bent toward a raised direction through the swinging of the raising bases 25 and 26 of the raising mechanisms 21 and 22, so that the treating tools are varied to those directions projecting from the distal end of the endoscope.

Figure 4:
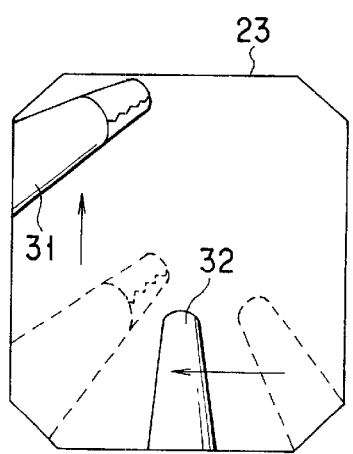
FIG. 4 is a view showing another image of an endoscope's visual field displayed on the TV monitor.

The first raising mechanisms 21 is so operated that the treating tool 31 situated on the lower left side in the endoscope's visual field image 23 as shown in FIG. 4, that is, on the lower right side in FIG. 1, and projected from the first treating tool insertion channel 14 is raised at a given angle toward an upper side in the endoscope's visual field image 23, that is, toward the upper right side in FIG. 1.

On the other hand, the second raising mechanism 22 is so operated that the treating tool 32 situated on the lower right side in the endoscope's visual field 23, that is, on the lower left side in FIG. 1, and projected from the second treating tool insertion channel 15 is raised at a given angle toward a lower left side in the endoscope's visual field image 23 and toward a lower right side in FIG. 1.

That is, these two raising mechanisms 21 and 22 are so operated as to raise the treating tools 31 and 32 in a direction substantially perpendicular to each other. For this reason, the axes of the pins for pivotally supporting the raising bases 25 and 26 of the raising mechanisms 21 and 22 are set substantially perpendicular to each other.

Further, the forceps raising mechanism 21 at the first treating tool insertion channel 14 is so set that its treating tool is raised to a greater variable extent than that of the forceps raising mechanism 22 at the second treating tool insertion channel 15 and its raising direction is so set as to be tilted to an outer side, though being slight as seen from an upper side on the endoscope's visual field image 23, that is, to a left side.

As evident from the above, the treating tools 31 and 32 projected from the treating tool insertion channels 14 and 15 of the endoscope 1 are raised by a proximal-side operation, that is, by moving the raising operation wires 28 and 29 back and forth by levers, etc., of a raising operation mechanism on the operation section, not shown. That is, grasping forceps, for example, as the treating tool 31 in FIG. 4 is raised upward at a given angle while, on the other hand, a cutting tool for example as the treating tool 32 is raised at a given angle in a lower right/left direction. In either case, the projecting direction can be adjusted individually independently.

The forceps raising mechanism 21 operating in the up/down direction is different from the forceps raising mechanism 22 operating in the right/left direction in terms of their raising operation amounts and, here, the former is greater in raising operation amount than the latter.

Although the endoscope 1 of the present embodiment has been explained mainly about the differences from the conventional endoscope, the other arrangements may be the same as those of the heretofore used endoscopes.

Figure 5:
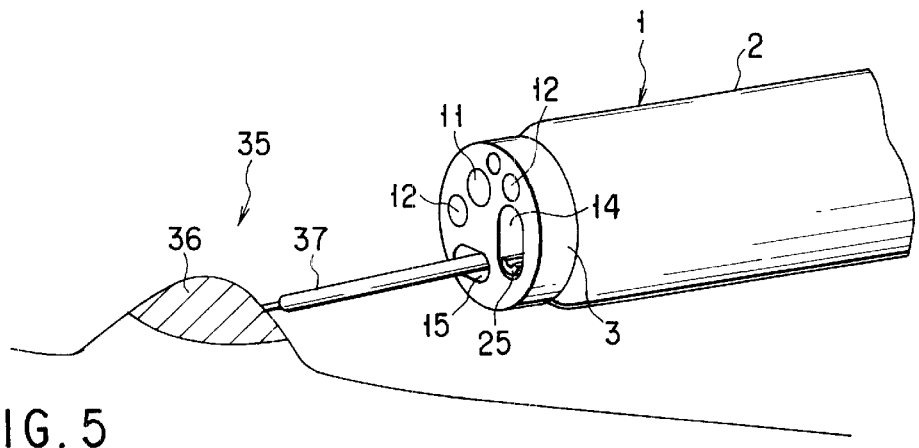
FIG. 5 is an explanative view showing a state of use of the endoscope.

Now an explanation will be made about the function of the thus arranged endoscope. As shown in FIG. 5, the insertion section 2 of the endoscope 1 is inserted into a body cavity 35 of a human subject, and an injection needle 37 is inserted via, for example, the second treating tool insertion channel 15 toward an affected mucosa while observing it under the endoscope 1. A liquid medicine, such as a physiological saline, is then injected by the injection needle 37 into an underlying layer of the affected mucosa 36 to cause a mucous layer, including the affected mucosa, to be raised.

Figure 6:
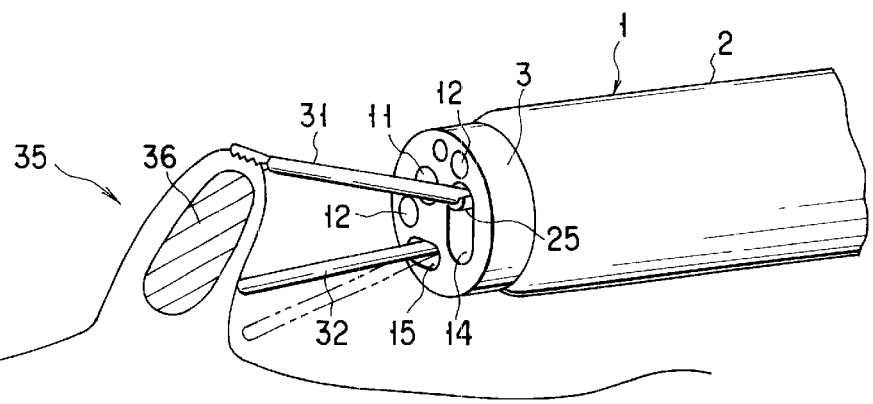
FIG. 6 is an explanative view showing another state of use of the endoscope.

Then, as shown in FIG. 6, a grasping treating tool (hereinafter referred to as grasping forceps) 31 is inserted into the body cavity 35 of the human subject via the first treating tool insertion channel 14 of the endoscope 1 and, via the second channel 15 through which a spent injection needle 37 was withdrawn, a cutting treating tool (hereinafter referred to as a cutting tool) 32, such as an electric surgical knife or laser probe, is inserted into the body cavity 35.

And, as shown in FIG. 6, the top portion of the affected mucosa 36 is grasped by the grasping forceps 31 and, while the grasping forceps 31 together with the grasped mucosa 36 is raised by the operation of the forceps raising mechanism 21, that lower portion of the grasped mucosa 36 is cut off by the cutting tool 32. That is, the raising mechanism 22 at the second treating tool insertion channel 15 is operated and, while the cutting tool 32 is swung in the right/left direction, the cutting of the grasped mucosa 36 or its lower layer portion is continued.

The operator, when performing this cutting operation, feels as if the grasped mucosa were raised by his or her own left hand and the raised mucosa region were cut with the cutting tool 32 manipulated by his or her own right hand, that is, as if these operations were reproduced on the distal end of the endoscope 1. Since, in performing this operation, the operator does not need to operate the distal end 3 of the endoscope 1 to a more-than-necessary extent, it is possible to continue the cutting operation easily while securing a better endoscope's visual field.

By using the thus structured endoscope and associated treating tools, the operator feels as if, while raising the grasped mucosa 36, the lower portion of the mucosa were cut off with the use of both his or her own hands. It is, therefore, possible to easily and positively perform the cutting operation on the affected mucosa region in the body cavity of the human subject. In addition, it is also possible to cut off a larger diseased tissue region as one mucosa region at a time and to solve the problem with a "partial cutting" of the diseased tissue.

It may be considered that the endoscope may be so constructed that the right and left treating tool insertion channels described above are positionally reversed. In this case, the cutting tool is inserted through the first treating tool insertion channel 14 and the grasping forceps is inserted through the second treating tool insertion channel 15 by which a cutting operation is done while adjusting these treating tool positions relative to a mucosa in the body cavity at the distal end of the endoscope.

Figure 7:
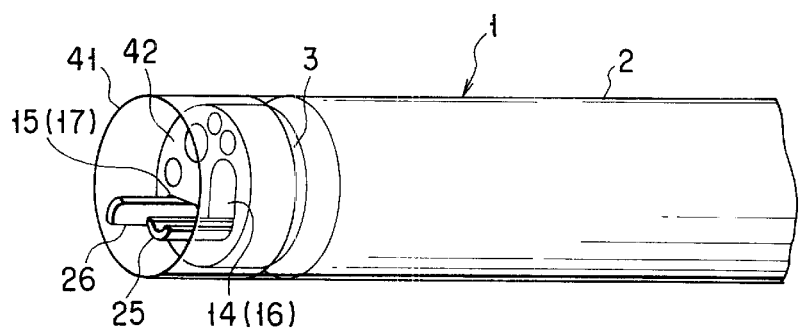
FIG. 7 is a perspective view showing a distal end and its neighboring area of an insertion section of an endoscope according to a second embodiment of the present invention.

With reference to FIG. 7, an explanation will be made below about the endoscope according to a second embodiment of the present invention.

This embodiment shows a modification of the first embodiment. In this endoscope, raising bases 25 and 26 constituting raising operation members of forceps raising mechanisms 21 and 22 are provided at distal end openings 16 and 17 of treating tool insertion channels 14 and 15, and the forward end portions of the raising bases 25 and 26 are so provided as to be projected forwardly of the endoscope's distal end face 42 from the distal end openings 16 and 17. An annular transparent hood 41 is fitted around the distal end 3 of the endoscope 1.

The projecting length of the hood 41 from the endoscope's distal end face 42 is set to be equal to, or greater than, the projecting length of the raising bases 25 and 26 of the raising mechanisms 21 and 22. The detailed construction common to that of the first embodiment and other constructions are the same as those of the above-mentioned first embodiment.

It is to be noted that, in the structure of this embodiment as shown in FIG. 7, the hood 41 is considered as being a detachable one adapted to be fitted over the distal end of the insertion section of the heretofore available endoscope, but that the hood 41 may be of such a type as to be made integral with, or fixed to, the distal end of the insertion section of the endoscope.

In the case where the insertion section 2 of the endoscope 1 is inserted into the body cavity of the patient, for example, into the esophagus or stomach through the mouth, since the raising bases 25 and 26 of the raising mechanisms 21 and 22 projected from the distal end face of the insertion section 2 are located inside the hood 41, the raising bases 25 and 26 are prevented from contacting with the inner surface of the body cavity even if these raising bases are projected from the distal end face of the insertion section.

In use, as in the case of the first embodiment, the grasping forceps is inserted into the first treating tool insertion channel 14 and the cutting tool is inserted through the second treating tool insertion channel 15 and an operation is performed on the affected mucosa through a resection treatment, etc. At this time, the grasping forceps for grasping the mucosa is raised while the projecting portion of the grasping forceps is supported by the raising base 25 of the raising mechanism 21 projected from the distal end of the endoscope's insertion section 2. Therefore, without the flexing the shaft portion of the grasping forceps 31 it is possible to greatly and strongly raise the mucosa tissue. The cutting tool, such as an electric surgical knife for cutting off the lower portion of the raised mucosa tissue and a contact-type laser probe, is raised while being supported by the raising base 25 of the raising mechanism 21, the mucosa tissue can be cut off positively.

According to the present embodiment, it is possible to easily and positively resect an affected mucosa in the body cavity as in the case of the first embodiment and it is also possible in the second embodiment, in particular, to not only properly raise the mucosa tissue but also accurately perform its cutting operation.

Figure 8:
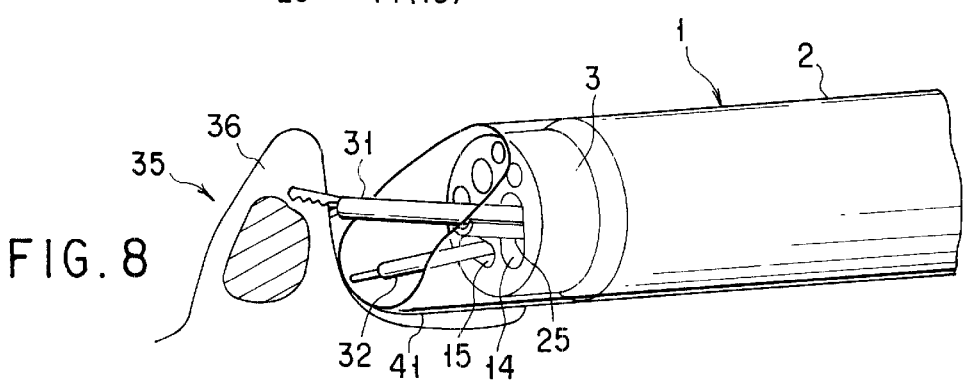
FIG. 8 is a perspective view showing a state of use of a distal end and its neighboring area of an insertion section of an endoscope according to a third embodiment of the present invention.

A third embodiment of the present invention will be explained below with reference to FIG. 8.

This embodiment has a modified raising mechanism of the second embodiment. That is, as shown in FIG. 8, this endoscope has a substantially obliquely-cut cylindrical hood configuration as a whole such that its forwardly extending larger portion is situated adjacent to two distal end openings 16 and 17 and continuously decreases its forwardly extending length toward an opposite side. In this case, the forwardly extending larger section adjacent to the distal end openings 16 and 17 is greater in length than the hood 41 of the second embodiment.

Even in this structure, raising bases 25 and 26 of forceps raising mechanisms 21 and 22 are projected from the distal end openings 16 and 17 of treating tool insertion channels 14 and 15 to such an extent that these raising bases are accommodated within the obliquely-cut cylindrical hood 41 and, desirably, the constituent members, such as the raising bases 25 and 26, are held within the obliquely-cut cylindrical hood over a whole operation range.

Since the hood 41 is provided as in the case of the second embodiment, the raising bases 25 and 26 of the forceps raising mechanisms 21 and 22 projected from the distal end of the endoscope 1 are safely guided without contacting with the mucosa in the body cavity and the cutting treatment of an affected mucosa 36 is carried out by the grasping forceps 31 inserted through the first treating tool insertion channel 14 and cutting tool 32 inserted through the second treating tool insertion channel 15.

According to this embodiment, the grasping forceps 31 inserted through the first treating tool insertion channel 14 is raised without being flexed by the raising base 25 of the forceps raising mechanism 21 projected from the distal end of the endoscope 1 as in the case of the second embodiment and it is, therefore, possible to greatly raise the affected mucosa 36 upwardly.

Further, the forwardly extending larger section of the hood 41 presses a tissue of near-side affected mucosa 36 to be grasped by the grasping forceps 31, so that the affected mucosa is more raised and it is easier to locate a desired cutting site cut by the cutting tool 32.

An advantage can be expected that the affected mucosa 36 to be cut by the raising of the mucosa by the grasping forceps 31 and pressing of the near-side mucosa surface by the hood 41 is mechanically separated. Farther, it is also expectable that it take less time to perform a cutting operation on the mucosa.

According to this invention, in addition to the advantage of the first and second embodiments, the hood 41 acts as an added imaginary operator's hand and serves to press against the near-side portion of the mucosa tissue and it is possible to more greatly upwardly raise a to-be-cut mucosa tissue by the grasping forceps. Further, is also possible to mechanically separate the mucosa tissue by the raising operation of the in a shorter time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion section having at least a first treating tool insertion channel and a second treating tool insertion channel, each having a distal end opening at a distal end of the insertion section for enabling at least respective first and second treating tools to be projected therefrom;
   a first mechanism provided at the distal end opening of the first treating tool insertion channel and having an operation member for changing a projecting direction of the first treating tool toward a first direction; and
   a second mechanism provided at the distal end opening of the second treating tool insertion channel and having an operation member for changing a projecting direction of the second treating tool toward a second direction different from the first direction.

2. An endoscope according to claim 1, wherein the distal end opening of the first treating tool insertion channel and the distal end opening of the second treating tool insertion channel are opened in substantially the same direction, and when the operation member of the first mechanism and the operation member of the second mechanism are in an initial standby position, the projecting direction of the first treating tool and the projecting direction of the second treating tool are substantially parallel to each other.

3. An endoscope comprising:
   an insertion section having at least a first treating tool insertion channel and a second treating tool insertion channel, each having a distal end opening at a distal end of the insertion section for enabling at least respective first and second treating tools to be projected therefrom;
   a first mechanism provided at the distal end opening of the first treating tool insertion channel and having an operation member for changing a projecting direction of the first treating tool toward a first direction; and
   a second mechanism provided at the distal end opening of the second treating tool insertion channel and having an operation member for changing a projecting direction of the second treating tool toward a second direction different from the first direction;
   wherein the first direction and the second direction are substantially orthogonal to each other.

4. An endoscope according to claim 3, further comprising means for moving images of the treating tools, included in an image obtained by the endoscope, in the same directions that the treating tools are moved.

5. An endoscope according to claim 4, wherein the first and second mechanisms are adapted to move the first and second treating tools by different operation amounts.

6. An endoscope according to claim 5, wherein the first mechanism is adapted to move the first treating tool in an up/down direction by a first operation amount, and the second mechanism is adapted to move the second treating tool in a right/left direction by a second operation amount which is less than the first operation amount.

7. An endoscope comprising:

an insertion section having at least a first treating tool insertion channel and a second treating tool insertion channel, each having a distal end opening at a distal end of the insertion section for enabling at least respective first and second treating tools to be projected therefrom;

a first mechanism provided at the distal end opening of the first treating tool insertion channel and having an operation member for changing a projecting direction of the first treating tool toward a first direction; and a second mechanism provided at the distal end opening of the second treating tool insertion channel and having an operation member for changing a projecting direction of the second treating tool toward a second direction different from the first direction;

wherein the first direction and the second direction are substantially orthogonal to each other; and wherein the operation member of the first mechanism and the operation member of the second mechanism are projected from the insertion section.

8. An endoscope according to claim 7, further comprising an annular hood provided on the distal end of the insertion section such that at least a portion of a periphery of the hood is further projected than the distal end of the insertion section.

9. An endoscope according to claim 8, wherein the hood has a longer peripheral section near to the distal end openings of the first and second treating tool insertion channels than at a remaining portion on an opposite side.

* * * * *